United States Patent
McDevitt

[19]

[11] Patent Number: 5,885,293
[45] Date of Patent: Mar. 23, 1999

[54] APPARATUS AND METHOD FOR CUTTING A SURFACE AT A REPEATABLE ANGLE

[75] Inventor: Dennis McDevitt, Upton, Mass.

[73] Assignee: Innovasive Devices, Inc., Marlborough, Mass.

[21] Appl. No.: 810,649

[22] Filed: Mar. 3, 1997

[51] Int. Cl.[6] .................................................. A61B 17/56
[52] U.S. Cl. ............................. 606/80; 606/79; 606/102
[58] Field of Search ................................ 606/102, 96, 97, 606/98, 86, 79, 80, 81, 82, 83, 84, 85, 87, 88

[56] References Cited

U.S. PATENT DOCUMENTS

| | | |
|---|---|---|
| Re. 34,293 | 6/1993 | Goble et al. . |
| Re. 34,871 | 3/1995 | McGuire et al. . |
| D. 368,777 | 4/1996 | Goble et al. . |
| D. 374,286 | 10/1996 | Goble et al. . |
| D. 374,287 | 10/1996 | Goble et al. . |
| D. 374,482 | 10/1996 | Goble et al. . |
| 3,577,979 | 5/1971 | van der Gaast . |
| 3,848,601 | 11/1974 | Ma et al. . |
| 4,059,115 | 11/1977 | Jumashev et al. . |
| 4,142,517 | 3/1979 | Stavropoulos et al. . |
| 4,293,962 | 10/1981 | Fuson . |
| 4,408,938 | 10/1983 | Maguire . |
| 4,559,936 | 12/1985 | Hill . |
| 4,649,918 | 3/1987 | Pegg et al. . |
| 4,708,132 | 11/1987 | Silvestrini . |
| 4,738,255 | 4/1988 | Goble et al. . |
| 4,782,833 | 11/1988 | Einhorn et al. . |
| 4,870,957 | 10/1989 | Goble et al. . |
| 4,871,289 | 10/1989 | Choiniere . |
| 4,873,991 | 10/1989 | Skinner . |
| 4,884,572 | 12/1989 | Bays et al. . |
| 4,898,156 | 2/1990 | Gatturna et al. . |
| 4,899,743 | 2/1990 | Nicholson et al. . |
| 4,901,711 | 2/1990 | Goble et al. . |
| 4,968,315 | 11/1990 | Gatturna . |
| 4,988,351 | 1/1991 | Paulos et al. . |
| 5,002,578 | 3/1991 | Luman . |
| 5,013,318 | 5/1991 | Spranza, III ............................ 606/102 |
| 5,046,513 | 9/1991 | Gatturna et al. . |
| 5,059,206 | 10/1991 | Winters . |
| 5,067,964 | 11/1991 | Richmond et al. . |
| 5,092,891 | 3/1992 | Kummer . |
| 5,102,421 | 4/1992 | Anspach, Jr. . |
| 5,116,337 | 5/1992 | Johnson . |
| 5,129,902 | 7/1992 | Goble et al. . |
| 5,139,520 | 8/1992 | Rosenberg . |
| 5,141,520 | 8/1992 | Goble et al. . |
| 5,152,763 | 10/1992 | Johnson . |
| 5,163,940 | 11/1992 | Bourque ..................................... 606/96 |

(List continued on next page.)

FOREIGN PATENT DOCUMENTS

| | | |
|---|---|---|
| 0530804 | 10/1993 | European Pat. Off. . |
| 0 611 557 | 8/1994 | European Pat. Off. . |
| WO 92 04874 | 4/1992 | WIPO . |
| WO 9307819 | 4/1993 | WIPO . |

*Primary Examiner*—Guy V. Tucker
*Attorney, Agent, or Firm*—Choate, Hall & Stewart

[57] ABSTRACT

A tool for cutting surfaces at repeatable angles relative to the surface being cut is provided. In one embodiment, the tool is used for cutting a bone in a direction perpendicular to a surface of the bone. The tool includes a cylindrical bone cutter having an operable portion located at a proximal end of the cutter for cutting bone. The bone cutter has an internal surface and the internal surface defines an internal bore extending along a longitudinal axis of the cutter from a proximal end to a distal end. A probe, slidably mounted within the bore of the cutter, extends beyond the operable portion of the cutter, and is biased towards the bone surface. An indicator coupled to the probe designates the position of the probe relative to the operable portion of the cutter. When the indicator is maximally displaced away from the proximal end of the cutter, while maintaining the probe and the cutter in contact with the bone surface, the longitudinal axis of the cutter will be substantially perpendicular to the surface of the bone. At this point of maximum displacement, force may be applied to the cutter to make a cut into the bone that is orthogonal to the bone surface. Methods for using the tool are also provided.

64 Claims, 11 Drawing Sheets

U.S. PATENT DOCUMENTS

| | | |
|---|---|---|
| 5,190,548 | 3/1993 | Davis . |
| 5,207,679 | 5/1993 | Li . |
| 5,224,946 | 7/1993 | Hyhurst et al. . |
| 5,234,434 | 8/1993 | Goble et al. . |
| 5,234,435 | 8/1993 | Seagrave, Jr. et al. . |
| 5,236,445 | 8/1993 | Hayhurst et al. . |
| 5,266,075 | 11/1993 | Clark et al. . |
| 5,268,001 | 12/1993 | Nicholson et al. . |
| 5,314,429 | 5/1994 | Goble et al. . |
| 5,341,816 | 8/1994 | Allen . |
| 5,350,380 | 9/1994 | Goble et al. . |
| 5,350,383 | 9/1994 | Schmieding et al. . |
| 5,352,229 | 10/1994 | Goble et al. . |
| 5,354,300 | 10/1994 | Goble et al. . |
| 5,358,511 | 10/1994 | Gatturna et al. . |
| 5,370,646 | 12/1994 | Reese et al. . |
| 5,380,334 | 1/1995 | Torrie et al. . |
| 5,385,567 | 1/1995 | Goble ............................................ 606/96 |
| 5,393,302 | 2/1995 | Clark et al. . |
| 5,397,356 | 3/1995 | Goble et al. . |
| 5,403,320 | 4/1995 | Luman et al. . |
| 5,417,692 | 5/1995 | Goble et al. . |
| 5,417,712 | 5/1995 | Whittaker et al. . |
| 5,423,824 | 6/1995 | Akerfeldt et al. . |
| 5,425,490 | 6/1995 | Goble et al. . |
| 5,431,651 | 7/1995 | Goble . |
| 5,458,601 | 10/1995 | Young, Jr. et al. . |
| 5,464,427 | 11/1995 | Curtis et al. . |
| 5,472,452 | 12/1995 | Trott . |
| 5,480,403 | 1/1996 | Lee et al. . |
| 5,486,197 | 1/1996 | Le et al. . |
| 5,489,210 | 2/1996 | Hanosh . |
| 5,496,326 | 3/1996 | Johnson . |
| 5,501,683 | 3/1996 | Trott . |
| 5,501,695 | 3/1996 | Anspach et al. . |
| 5,515,861 | 5/1996 | Smith . |
| 5,522,845 | 6/1996 | Wenstrom, Jr. . |
| 5,545,180 | 8/1996 | Le et al. . |
| 5,562,671 | 10/1996 | Goble et al. . |
| 5,569,252 | 10/1996 | Justin et al. . |
| 5,571,104 | 11/1996 | Li . |
| 5,578,037 | 11/1996 | Sanders et al. ............................ 606/80 |
| 5,643,273 | 7/1997 | Clark ........................................ 606/96 |
| 5,658,293 | 8/1997 | Vanlaningham ........................ 606/88 |

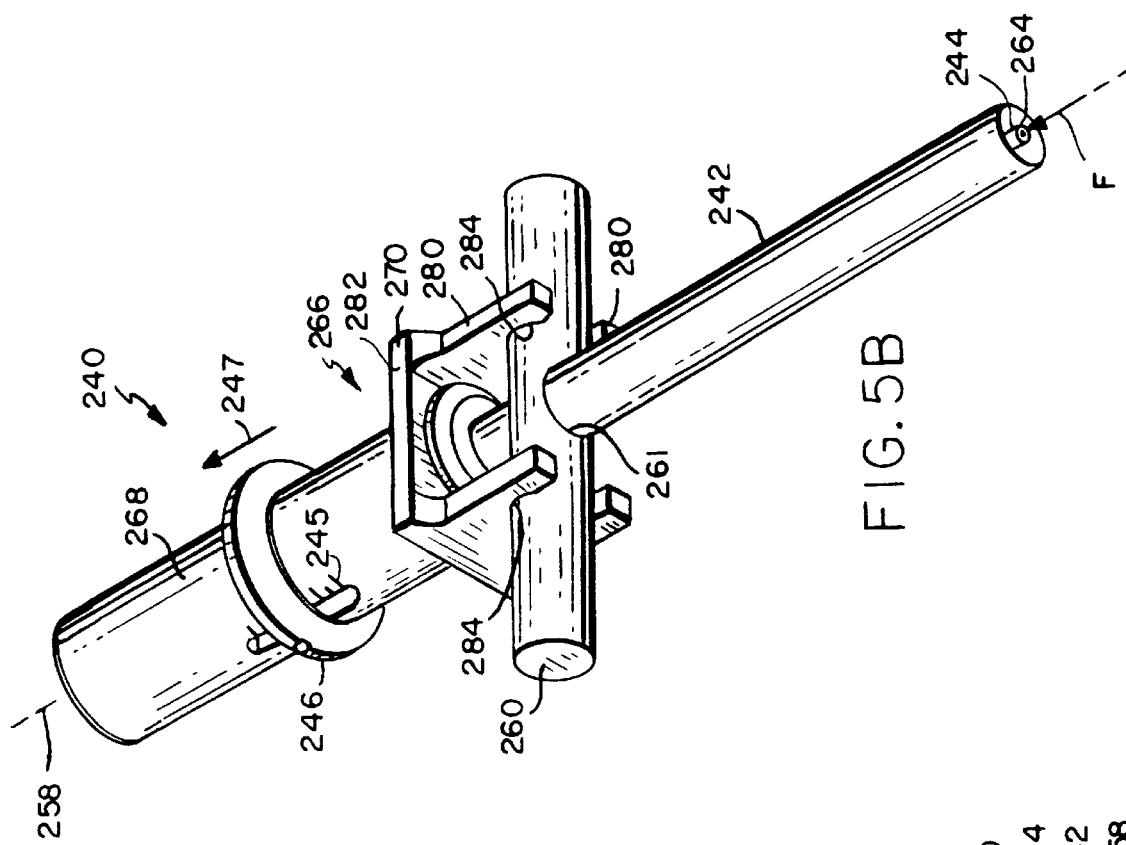
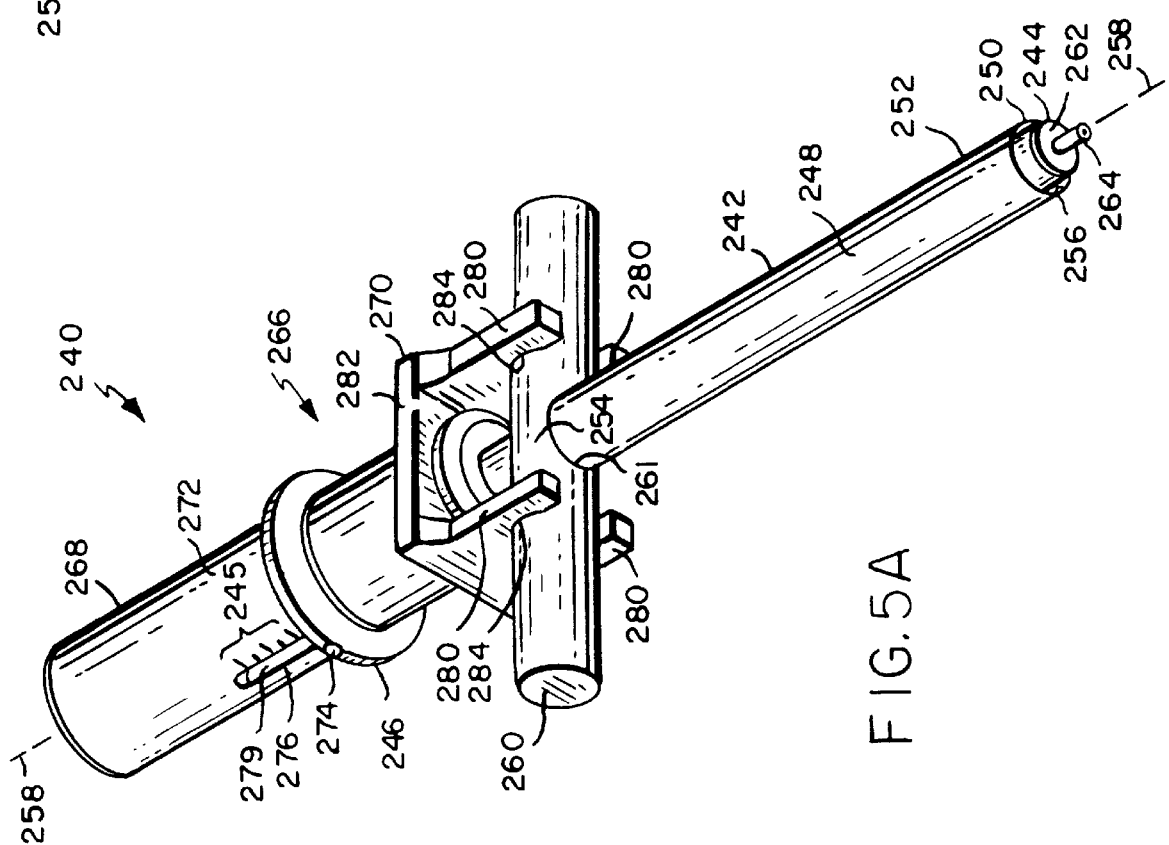

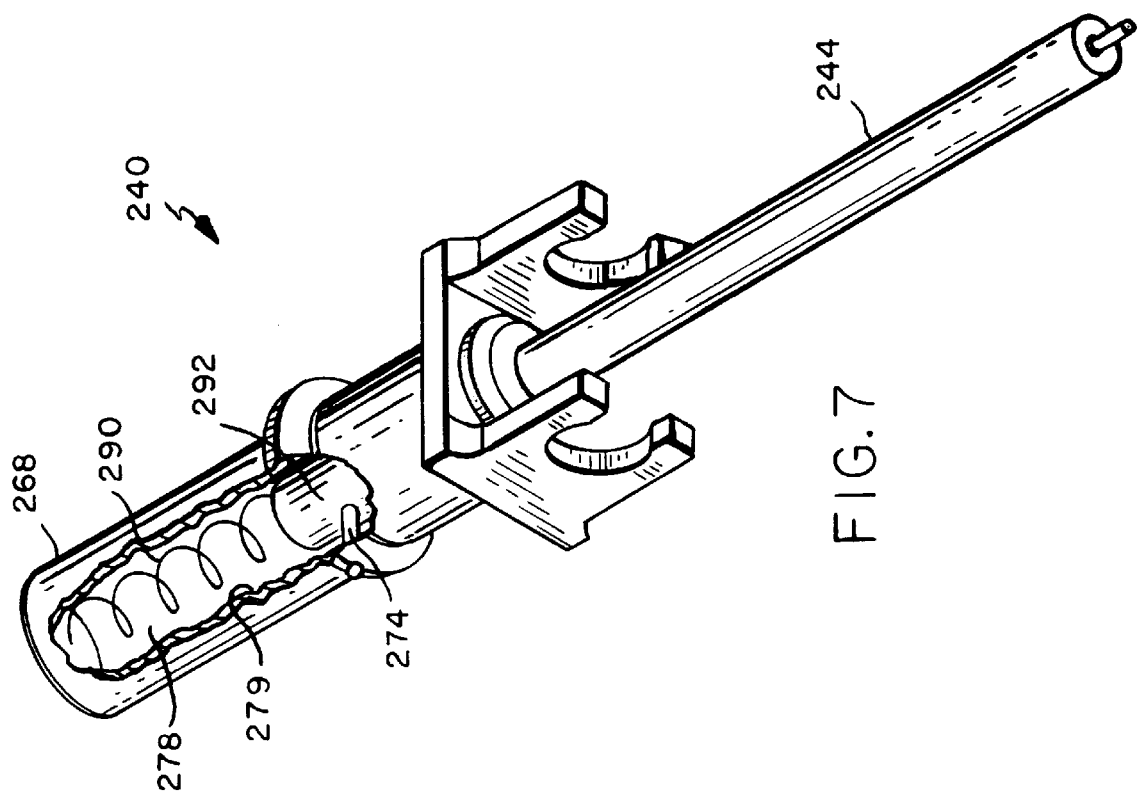
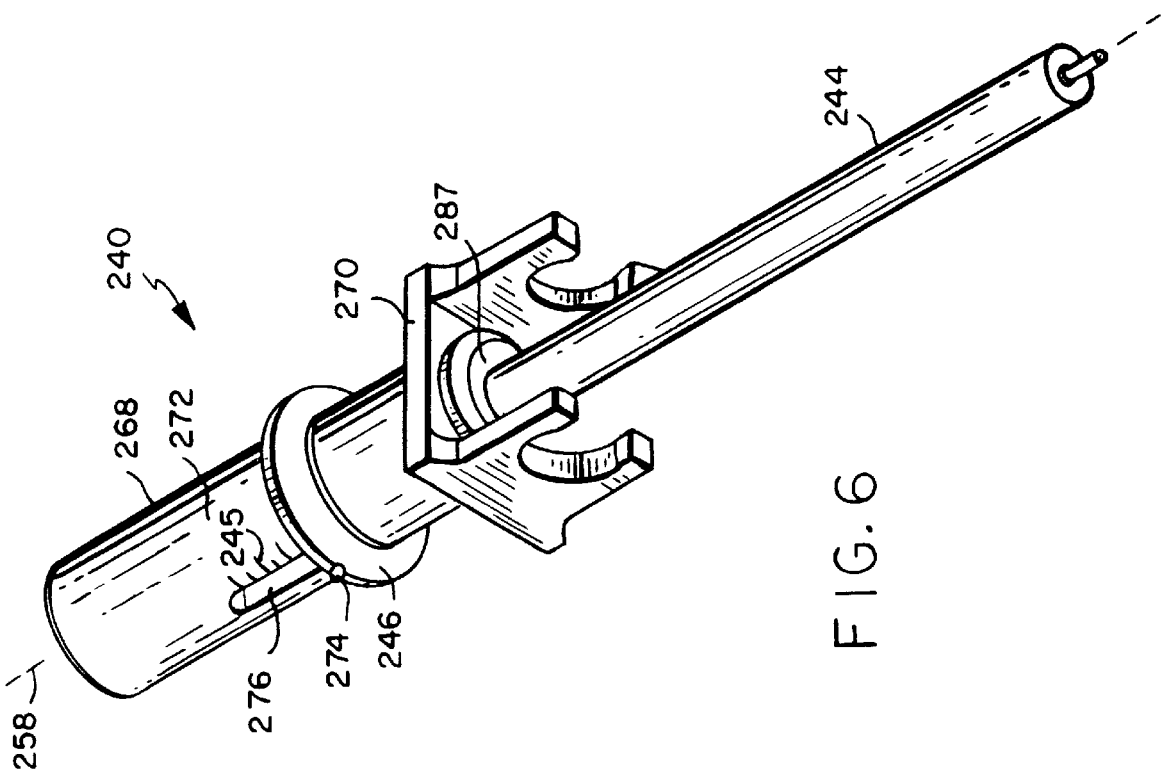

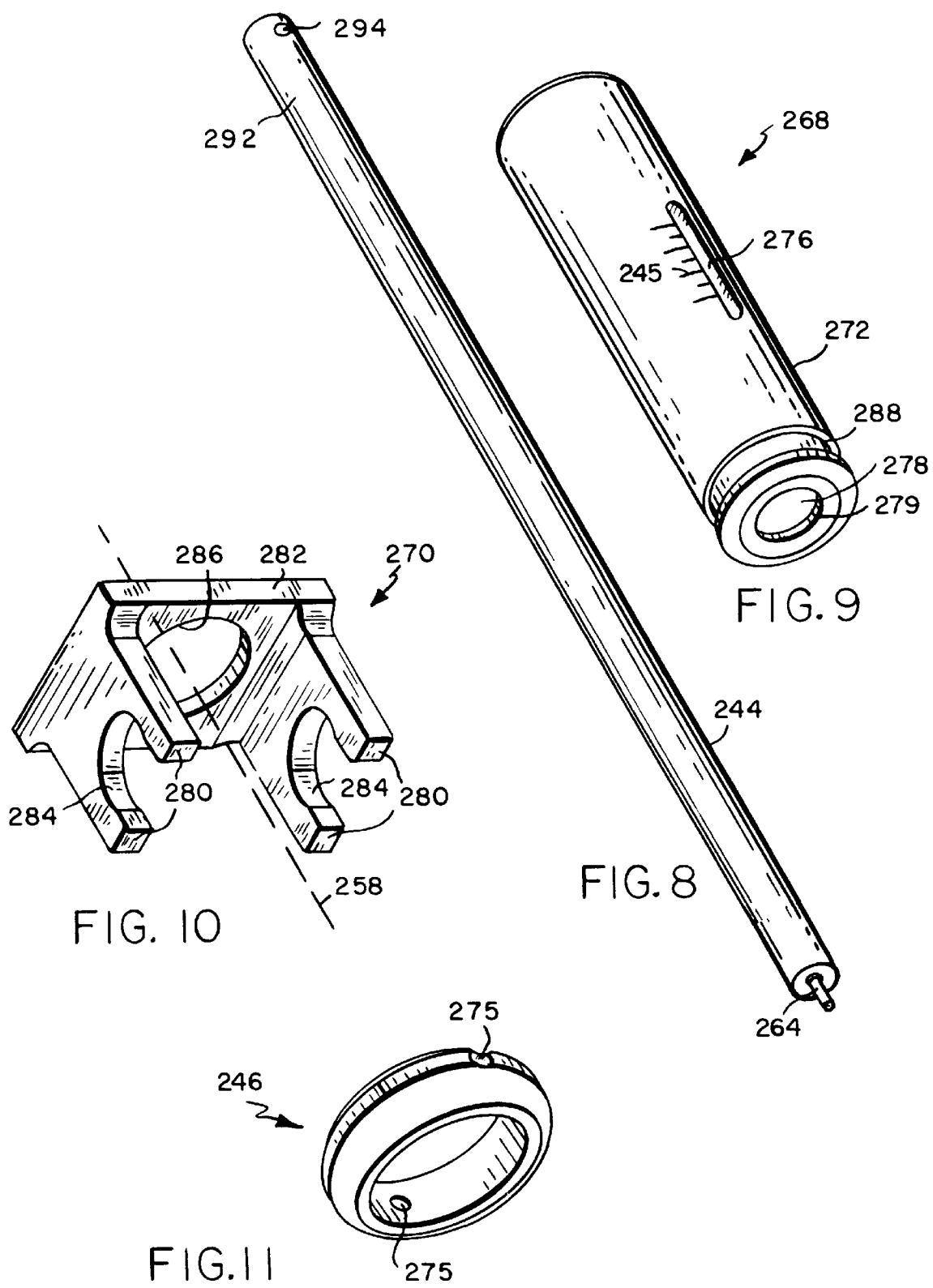

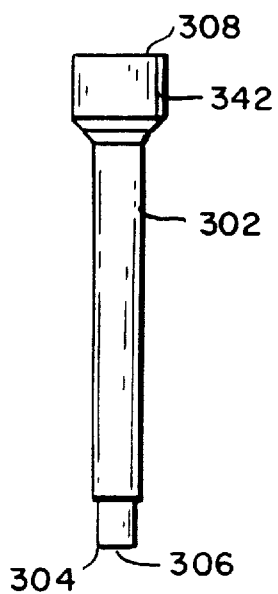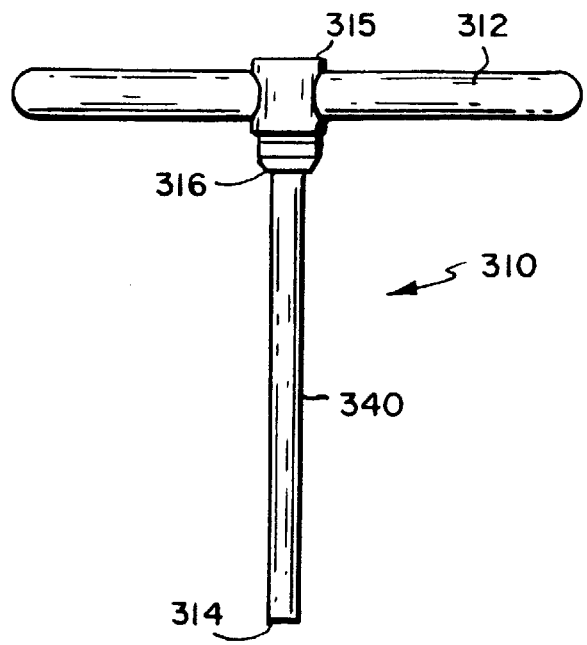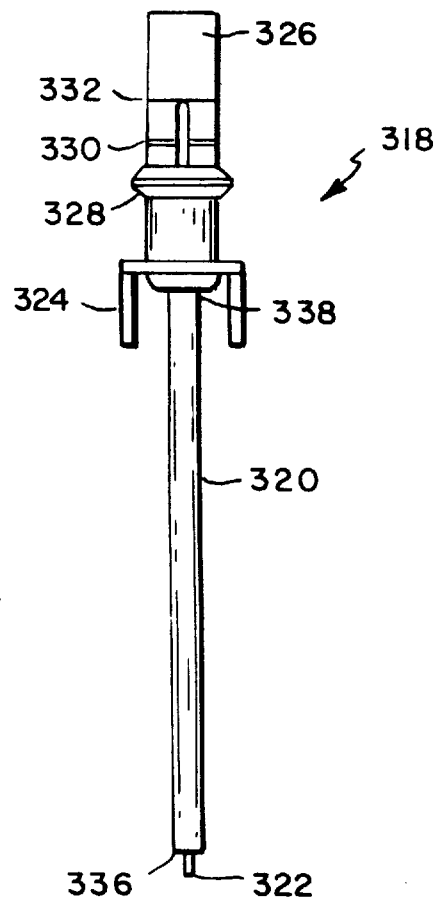

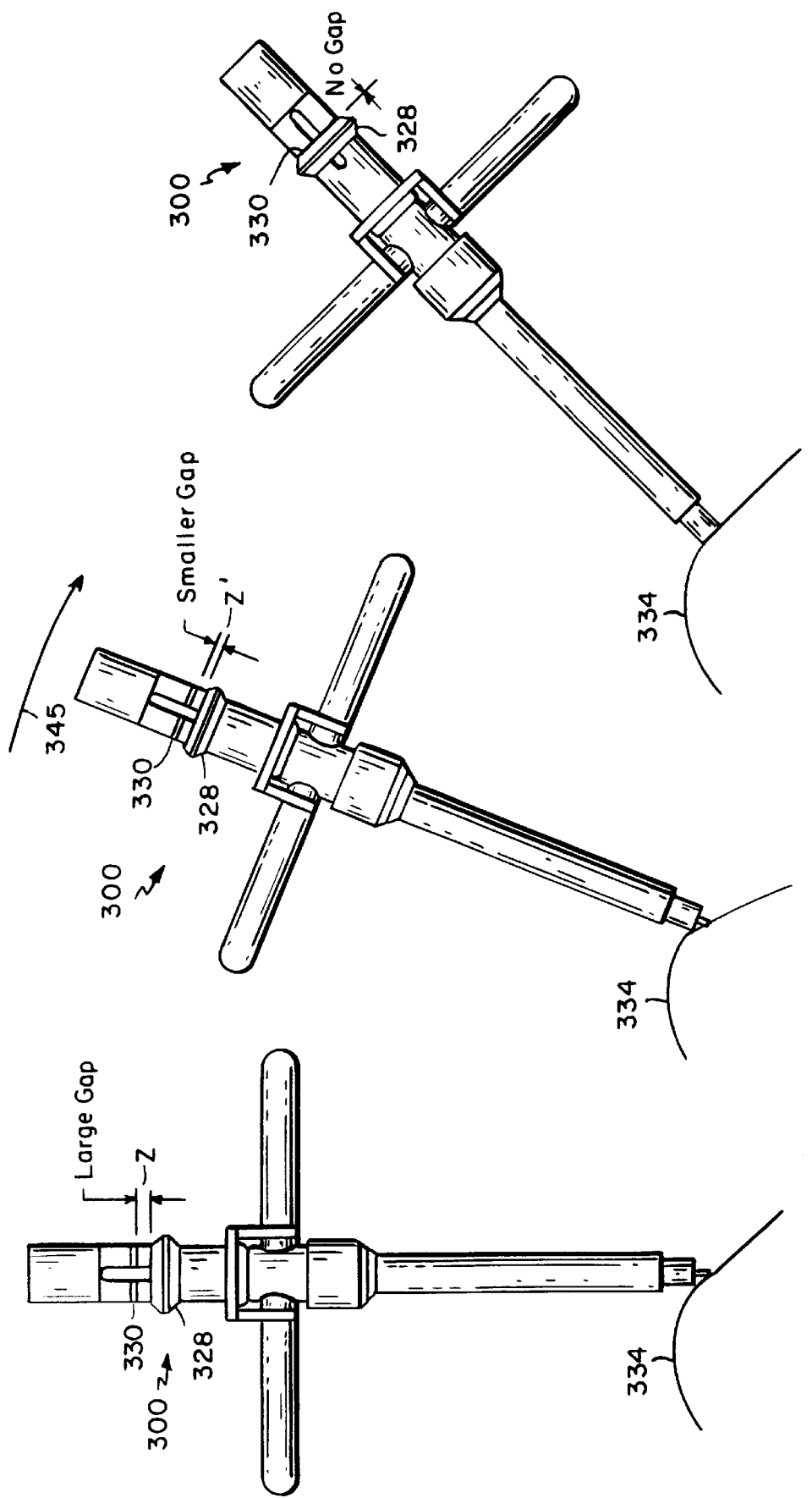

APPARATUS AND METHOD FOR CUTTING A SURFACE AT A REPEATABLE ANGLE

FIELD OF THE INVENTION

The present invention generally relates to methods and apparatus for cutting surfaces at repeatable angles relative to the surface being cut and the present invention more particularly relates to methods and apparatus for cutting bone at a repeatable angle with respect to a bone surface during articular cartilage defect repair.

BACKGROUND OF THE INVENTION

Defects in articular cartilage associated with trauma and osteochondritis dissecans are difficult for surgeons to repair. The patient can expect to face progressive deterioration over time leading to advanced osteochondritis, arthritis and the possibility of joint replacement. The knee as a weight-bearing joint is particularly susceptible to this problem, although similar injuries to the articular cartilage of other joints in humans and other mammals also occur with regularity.

FIG. 1 illustrates a knee joint 10 between the distal end 11 (i.e., that surface farthest from the center of the body) of a femur 12 and the proximal end 13 (i.e., that surface closest to the center of the body) of the tibia 14. Portions 15, 17 of the connective tissue which movably ties the femur 12 to the underlying tibia 14 and fibula 18 are shown. Normally interposed between opposing surfaces of the femur 12 and tibia 14 are lateral and medial meniscus cartilages, 21 and 23, respectively. The condyles 22 at the distal end 11 of the femur 12 are normally supported by the meniscus cartilages 21 and 23 on the proximal end 13 of the tibia 14. Normally, the distal end 11 of femur 12, including the condyles 22 is covered by a layer 28 of cartilaginous material about 5 mm thick, referred to as the articular cartilage. Articular cartilage 28 forms a generally resilient pad which is fixed on the distal surface 11 of the femur 12 to protect the femur from wear and mechanical shock. The articular cartilage 28, when lubricated by fluid in the knee joint 10, provides a surface which is readily slidable on the underlying surfaces of the meniscus cartilages 21 and 23 or on the proximal surface 13 of the tibia 14 if one or both of the meniscus cartilages 21, 23 should be partially or totally absent. Nevertheless, the articular cartilage 28 may become damaged in that it may be torn 24 or holed or become excessively worn.

Methods have been used to repair such articular cartilage damage before it can spread or result in eventual injury or wear to the underlying condyles 22, meniscus cartilages 21, 23, or tissues associated with the tibia 14. It has been known to replace damaged articular cartilage with a layer of fibrous material. See U.S. Pat. No. 5,067,964, incorporated herein by reference. Repairing defects in articular cartilage in human or other mammalian joints therefore requires materials that have been approved by the FDA for use in the human body. It is often problematic to find such materials that are commercially available and relatively low in cost in which completion of the repairs are within the skills of qualified orthopedic surgeons. Another repair method involves packing an articular cartilage defect with bits of cancellous and cortical bone (Soviet Patent SU 1454423, Jun. 27, 1986, incorporated herein by reference) that have been chipped from defect-free bone. This latter technique avoids using foreign materials but, like the former methods, does not preserve the original orientation of bone and cartilage.

Prostheses have also been used for replacement of the joint itself. Problems encountered after implanting such prostheses are usually caused by the cements used to attach the prostheses to the host bone. Further, some prostheses associated with joint replacements are actually much larger than the degenerated tissue that needs to be replaced so that extensive portions of healthy bone are typically removed to accommodate the prostheses.

A vastly improved method and apparatus for cartilage repair is disclosed in a copending and commonly owned patent application entitled "Apparatus and Methods for Articular Cartilage Defect Repair", filed Mar. 7, 1995 and assigned U.S. application Ser. No. 08/399,428, the entire contents of which are incorporated herein by reference. U.S. application Ser. No. 08/399,428 discloses an apparatus and method for drilling out damaged cartilage and replacing the damaged portion with healthy cartilage from another part of the body. A section of the damaged cartilage and the bone thereunder is drilled-out. A bone plug, with healthy cartilage attached to its surface, is cut from another section of bone and then inserted into the drilled-out section of the damaged cartilage. The new bone plug with healthy cartilage provides a solution to the cartilage repair problem.

While the method and apparatus for cartilage repair disclosed in U.S. application Ser. No. 08/399,428 is an improvement over the prior art, a difficulty remains in that the healthy cartilage attached to the bone plug should be in registration with the remaining cartilage in the damaged cartilage area. In other words, the new healthy cartilage should be at the same level as the surrounding cartilage. To accomplish this, the drilled-out portion should be drilled at the same angle and size as the healthy bone plug. Otherwise, for example, if the healthy bone plug is cut at an angle, when it is inserted into a damaged area where the drilled-out portion is normal to the bone surface the healthy cartilage will not properly register with the surrounding cartilage and the repair may be unsuccessful or of limited success. During many bone cutting operations, the surgeon cannot directly see the surface of the bone to ensure that a bone cutter is correctly orientated with respect to the bone surface. Thus, the need remains to develop an apparatus and method which cuts bone at a repeatable orientation with respect to the bone surface.

SUMMARY OF THE INVENTION

The present invention provides methods and apparatus for cutting objects or surfaces at repeatable angles relative to the object or surface being cut. For example, the present invention provides an apparatus for repairing articular cartilage defects that cuts bone at a repeatable angle (and preferably at a right angle) with respect to a bone surface. The present invention also provides for methods of using the apparatus.

In one embodiment of the invention, a tool for cutting bone that includes a bone cutter having an operable portion for cutting a bone is provided. A probe is slidably disposed relative to the cutter for contacting a surface of the bone in a region near the operable portion of the bone cutter. An indicator is coupled to the probe and designates the level of the surface of bone contacted by the probe relative to a surface of bone contacted by the operable portion of the cutting element. The indicator indicates the relative displacement between the probe and the cutter while both are in contact with the bone surface. In a preferred embodiment, the probe includes a tip which extends beyond the operable portion of the cutter. In another embodiment, a biasing mechanism, such as a spring or the like, is coupled between the cutter and the probe to bias the probe towards the bone surface.

The invention also pertains to a method of cutting a bone substantially perpendicular to a surface of the bone. The method includes the step of placing a tool for cutting bone in contact with the bone surface. The tool placed in contact with the bone surface includes a bone cutter having an operable portion for cutting bone, a probe that is slidable with respect to the cutter, and an indicator coupled to the probe for indicating the relative displacement between the probe and the cutter. The method also includes ensuring that the operable portion of the cutter is in contact with the bone surface, and ensuring that the probe is in contact with a bone surface in a region of the operable portion of the cutter. The tool is then adjusted, while keeping the cutter and the probe in contact with the bone surface, such that the probe is displaced relative to the cutter. The tool is then oriented to maximize the displacement of the indicator relative to the bone surface. Force may then be applied to the cutter to cut the bone substantially perpendicular to the bone surface.

The foregoing has outlined some of the more pertinent objects of the present invention. These objects should be construed to be merely illustrative of some of the prominent features and applications of the invention. Many other beneficial results can be attained by applying the disclosed invention in a different manner of modifying the invention as will be described. Accordingly, other objects and a fuller understanding of the invention may be had by referring to the following Detailed Description of the Invention.

BRIEF DESCRIPTION OF THE DRAWINGS

For a more complete understanding of the present invention, reference is had to the following description taken in conjunction with the accompanying drawings, in which:

FIG. 2A is a cross section through a bone that contains a defect in the articular cartilage.

FIG. 2B is a cross section through a bone whose defective cartilage area has been removed and into which a bone hole has been drilled. A bone plug is illustrated in proper orientation for insertion.

FIG. 2C illustrates a bone plug received within a drilled bone hole.

FIG. 2D illustrates a plurality of drilled bone holes within an articular cartilage defect.

FIG. 5A is an isometric view of a tool for cutting bone in accordance with the present invention.

FIG. 5B is an isometric view of the tool of FIG. 5A wherein a probe is displaced with respect to a bone cutter according to the present invention.

FIG. 6 is an isometric view of the tool of FIG. 5A with a bone cutter removed.

FIG. 7 is an isometric view of the tool of FIG. 5A with a partial sectional view.

FIG. 8 is an isometric view of a probe according to the present invention.

FIG. 9 is an isometric view of a cylinder according to the present invention.

FIG. 10 is an isometric view of a clip according to the present invention.

FIG. 11 is an isometric view of an indicator according to the present invention.

FIGS. 14A–14G illustrate an alternative embodiment of a tool suitable for use in accordance with the invention.

DETAILED DESCRIPTION OF THE INVENTION

Figure 1:
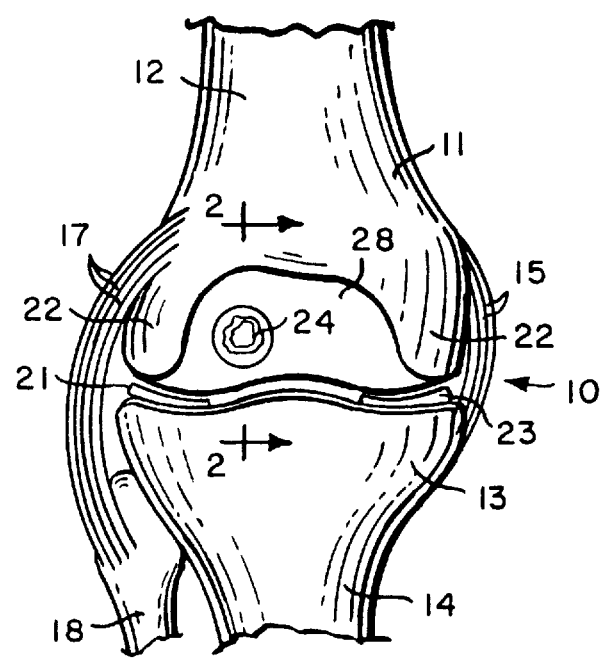
FIG. 1 is a fragmentary front elevation view of a human knee joint with sufficient tissue removed to show the articular cartilage on the condyles of the femur, and further showing a damaged area in the articular cartilage.
Figure 2A:
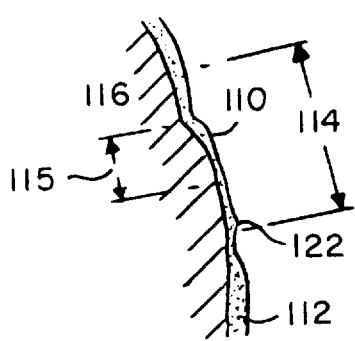
FIGS. 2A through 2D are cross-sectional views of a fragment of bone through section 2—2 of FIG. 1 illustrating the orientation of the bone hole and bone plug suitable for use in the invention.

Referring generally to FIGS. 2A through 2D, the present invention contemplates repairing a defect or damaged area 110 in an articular cartilage 112 by removing a conveniently shaped (for example circular) portion 114 of the defective articular cartilage layer 112 and a portion 115 of the underlying bone 116. FIG. 2A illustrates the general principle, discussed more fully below, that the surface area of the bone portion 115 removed is not necessarily co-extensive with the surface area 114 of cartilage removed. The edges 122 of the defect 110 are debrided to create vertical walls and sharp edges. The base of the defect is shaved smooth but is not abraded through to the subchondral bone. The size of the removed portion 114 is kept to a minimum, but is large enough to include the whole of the damaged cartilage area.

The bone may be drilled with a cannulated hand or power drill containing a drill bit that preferably has an expanded outside diameter (i.e., a depth stop countersink) located some distance distal to the proximal end of the drill bit. An exemplary drill bit used with the present methodology has a cutting surface exactly equal to the chosen length of the bone plug. That is, the cutting surface can be between about 5 mm and 15 mm in length. The outside diameter of such an exemplary drill bit is very slightly undersized relative to the inside bore diameter of the bone core removal tool. In particular, an internal bore of 0.196 (4.97 mm) inside diameter for the cylindrical cutting element of a bone core removal tool would require a drill bit of 0.190 (4.82 mm) inches outside diameter. The difference of 0.006 (0.15 mm) inches is necessary for the required interference fit of the bone plug within the drilled bone hole. The outside diameter of the drill bit begins its expanded depth stop section at a distance above the proximal end that is equal to the depth of the bone plug. This non-cutting portion of the expanded section may be 0.25 inches (6.35 mm) in diameter and can be about 6 inches (152.4 mm) long.

Bone holes drilled into the underlying bone may be of any depth but are preferably about 5 mm to about 15 mm in depth. It is desirable that excised plugs of articular cartilage with the underlying subchondral cancellous bone attached have a total length of about 10 mm. This will provide individual bone plugs having about 5 mm of cartilage and 5 mm of bone or other similar combinations such as 2 mm of cartilage and 8 mm of bone, 3 mm of cartilage and 7 mm of bone, etc.

Figure 3:
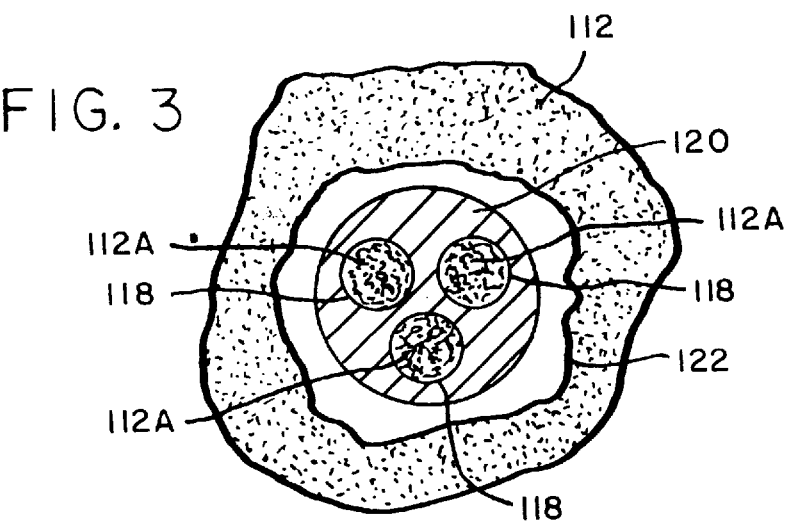
FIG. 3 is a front elevation view of a plurality of bone plugs received within a single drilled bone hole within an articular cartilage defect.

Depending on the size of the defect and of the underlying bone hole, several bone holes may be drilled, each bone hole designed to receive a single bone plug (see, e.g, FIG. 2D) or a single bone hole may be drilled to receive a plurality of bone plugs (see, e.g., FIG. 3).

Figure 2B:
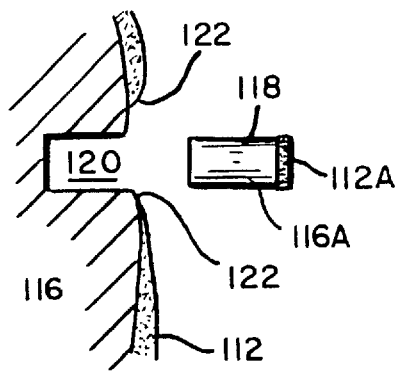
Figure 2C:
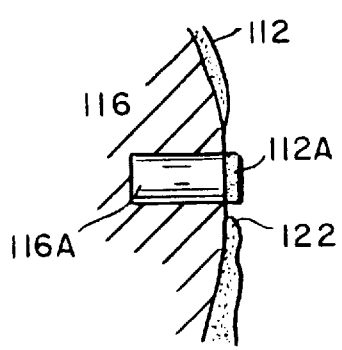
Figure 2D:
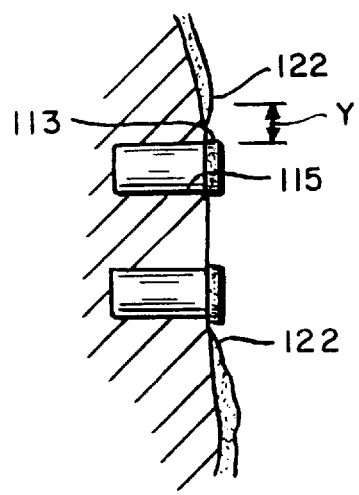

Following removal of the articular cartilage portion of the damaged area 110, as well as the underlying bone, a correspondingly sized and shaped bone plug 118 is inserted, first into and through the opening 114 left in the articular cartilage layer 112, and then into the underlying drilled bone hole 120 (see FIG. 2B). The bone plug 118 contains both bone 116A and its overlying articular cartilage 112A. These plugs will preferably be taken from the non weight-bearing surfaces of the joint principally in the intracondylar notch and the periphery of the condyle. The bone plug 118 is inserted into the drilled bone hole 120 so that the articular cartilage layer 112A of bone plug 118 is in lateral registration with (i.e., is aligned with) the articular cartilage layer 112 surrounding the drilled bone hole 120 (see FIG. 2C).

The bone plug 118 is of sufficient shape to maintain a frictional fit within the drilled bone hole 120 and will remain there until such time as tissue ingrowth from the surface of the bone and peripheral, cut edges 122 of the articular cartilage layer 112 surrounding the bone hole 120 more permanently fix the bone plug 118 in place.

Bone plugs 118 may be positioned within a single bone hole 120 so that their respective outer peripheral edges are not in contact with each other. Typically, individual bone plugs 118 located in their respective bone holes 120 may have their centers between 3 mm and 5 mm apart (see FIG. 2D). The peripheral edges 113, 117 of a given bone plug 118 are positioned at some distance (Y and Y', respectively) from the cut edges 122 of the defect.

These rules for bone plug spacing and orientation allow for a variety of possible configurations. For example, an articular cartilage defect 10 mm in diameter may accommodate one 5 mm diameter plug in the center of the defect. A defect 20 mm in diameter may be divided into four, 10 mm diameter quadrants and four holes drilled in the underlying bone. The defect therefore receives a total of four bone plugs.

Although the bone plug 118 is designed to have a friction fit into the drilled bone hole 120, several temporary fixation techniques are available. One such technique involves sewing sutures through the respective peripheral edges 113 of the articular cartilage layer 112A adhering to the bone plug and the articular cartilage 122 of the surrounding tissue. Alternatively, an adhesive layer (not shown) may be provided between the bone plug 118 and drilled bone hole 120. This adhesive layer allows time for sufficient ingrowth of tissue from the surrounding environment so that bone plug is locked into place in the bone hole. Various bio-adhesives are well known in the art. See, e.g., U.S. Pat. No. 5,067,964 (fibrinogen and thrombin sealant). The entire contents of U.S. Pat. No. 5,067,964 are incorporated herein by reference. Bone growth or cartilage growth promoting chemical factors may also be added. These may include cartilage-derived growth factor (CDGF—see U.S. Pat. No. 5,376,636, incorporated herein by reference), various inteleukins, colony-stimulating factor (CSF), osteopontin, platelet-derived growth factor (PDGF) and bone morphogenic protein (BMP-1). See also, U.S. Pat. No. 5,373,503, incorporated herein by reference.

Figure 4A:
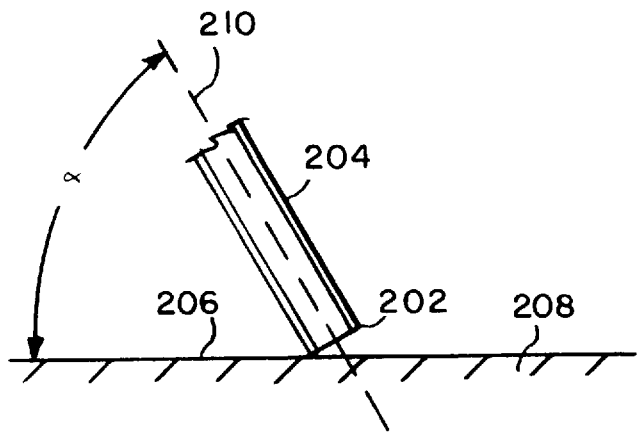
FIGS. 4A through 4C depict cross-sectional views of a bone cutter and a bone surface.
Figure 4B:
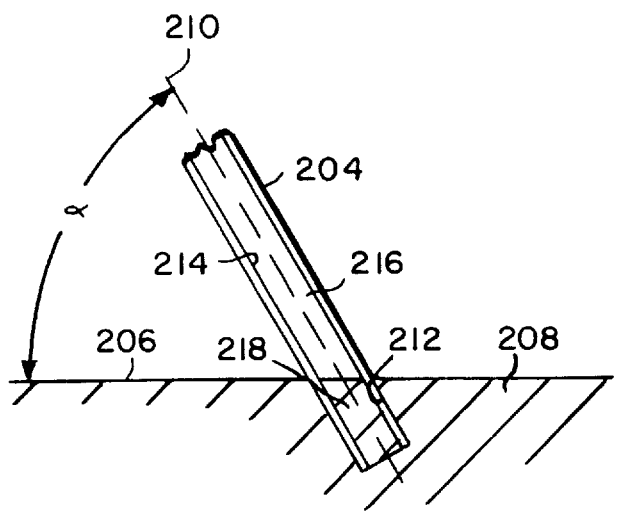
Figure 4C:
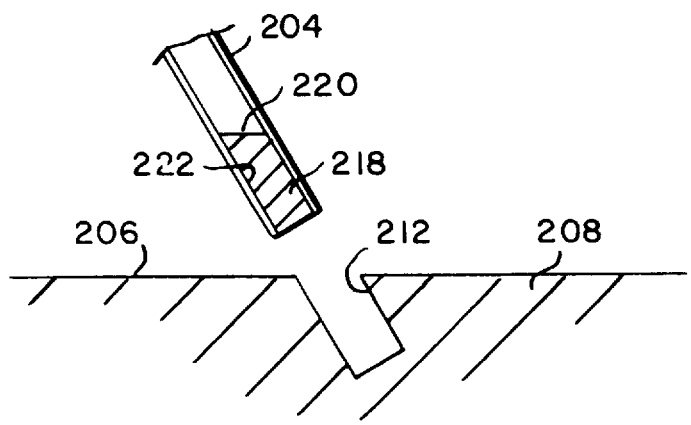

Referring now to FIGS. 4A through 4C, cross sectional views of a bone cutter and a bone surface are illustrated. As shown in FIG. 4A, a cutting edge 202 of a cutter 204 is in contact with a bone surface 206 of bone 208. As used herein, "bone surface" means the surface of the actual bone or it means the surface of material attached to the bone such as cartilage. Depicted in FIGS. 4A through 4C, is a longitudinal axis 210 of cutter 204 that is not perpendicular with respect to the bone surface 206. Often, a bone cutting procedure is preformed without the surgeon being able to see the bone surface 206. Under these circumstances (without being able to see the bone surface 206), even though the cutter 204 is in contact with the bone surface 206, the cutter 204 may be oriented at an another angle α that is not normal to the bone surface 206.

As shown in FIG. 4B, the cutter 204 enters the bone 208 at the angle α with respect to the bone surface 206 and a hole 212 is cut. The cutter 204 may have an inner surface 214 which defines a bore 216. It can be seen in FIG. 4B that a bone plug 218 cut by the cutter 204 is accepted in the bore 216. When the cutter 204 is removed from the bone 208, as shown in FIG. 4C, the hole 212 is not orthogonal to the bone surface 206. Furthermore, the bone plug 218 that is removed from the hole 212 does not have a top surface 220 that is perpendicular to its sides 222. Thus, if this bone plug 218 is placed in another hole (such as hole 120 in FIG. 2B) to effectuate a repair of damaged cartilage as described above, the top surface 220 of the plug will not be in registration with (or will not be at the same level as) the surrounding surfaces, unless the hole into which it is placed is cut at the same angle (and rotational orientation) as the plug 218. Misregistration may result in a failed cartilage repair and may also cause greater damage to the repair site than that which was originally present.

FIG. 5A illustrates a tool for cutting bone in accordance with the present invention. The tool 240 depicted in FIG. 5A provides a mechanism for cutting into the bone surface at a repeatable angle, and preferably at an angle that is perpendicular to the bone surface. The tool 240 includes a cutter 242, a probe 244 and an indicator 246. The cutter 242 depicted in FIG. 5A has a cylindrical body 248 which culminates in a cutting portion 250 at a proximal end 252 thereof. The cylindrical body 248 has an inner surface (not shown) that runs from the proximal end 252 to a distal end 254 of the cutter 242. The inner surface defines a bore 256 which runs the longitudinal length of the cylindrical body 248. The bore 256 is preferably coaxial with a longitudinal axis 258 of the cylindrical body 248. At the distal end 254 of the cutter 242, there is a handle 260 extending perpendicularly from the cylindrical body 248. The handle 260 enhances operability of the cutter 242, especially if the cutter 242 is to be rotated upon insertion into a bone (if the cutter 242 and handle 260 are formed of distinct units or pieces, handle 260 includes a hole or bore 261 such that cutter 242 can be connected to handle 260 as shown). Of course, it should be readily understood that the cutter 242 may be any of a multitude of other shapes and configurations. For example, the cutter may be a mechanical drill, may be non-cylindrical, or may not have a bore extending along its longitudinal length.

The probe 244 is preferably cylindrical and is mounted in the bore 256 of the cutter 242. The probe 244 is slidable, preferably along the longitudinal axis 258 of the cutter 242, and a proximal end 262 of the probe 244 extends out beyond the cutting portion 250. The proximal end 262 of the probe has a tip 264 which is coaxial with the cutter longitudinal axis 258. In a preferred embodiment, the tip 264 has a diameter less than 0.060 inches (1.52 mm) and extends beyond the proximal end 262 by at least 0.150 inches (3.18 mm).

The indicator 246 is mounted on a housing 266. As shown in the embodiment of FIG. 5A, housing 266 is directly attached to the handle 260 of the cutter 242, and the housing 266 includes a cylinder 268 and a clip 270. The indicator 246 is preferably a hollow ring slidably mounted around an outside surface 272 of cylinder 268. The cylinder 268 is directly attached to the clip 270 (for example, by engagement of cavity 288 as shown in FIG. 9 with clip 270) which in turn connects the housing 266 to the cutter 242. Thus, the cylinder 268, the clip 270 and the cutter 242 are directly coupled.

The indicator 246 is connected to the probe 244 with a pin 274 that extends through a longitudinal slot 276 in cylinder 268 and that extends through a hole or holes 275 in indicator 246 (as shown in FIG. 11). It will be appreciated that in an alternative embodiment, pin 274 can extend through two longitudinal slots 276 in cylinder 268 (and through holes 275 in indicator 246). In this embodiment, the longitudinal slots are positioned opposite one another around the cylinder 268. In another alternative embodiment, two or more pins may be employed. In this configuration, each pin extends through a corresponding longitudinal slot 276 in cylinder 268, through a corresponding hole 275 in indicator 246, and through a corresponding hole 294 in probe 244 (see FIG. 8).

The cylinder 268 has an internal cavity 278 (see FIG. 7) defined by internal walls 279 which permit the probe 244 to move within the cylinder 268. When the probe 244 slidably moves relative to the cutter 242, the indicator 246 correspondingly moves along cylinder 268 indicating the relative displacement between the probe 244 and the cutter 242. As discussed herein, the movement of indicator 248 can be measured and the measurement(s) used as appropriate.

Turning to FIG. 5B, the tool 240 is shown with the probe 244 displaced relative to the cutter 242 (and relative to the orientation in FIG. 5A) by a force F. The probe 244, in turn, displaces the indicator 246 along the cylinder surface 272 in the direction of arrow 247. The indicator 246 shows the relative displacement between the probe 244 and the cutter 242. It should be understood that the indicator can be oriented and/or shaped in many other alternative configurations. For example, the indicator need not be ring shaped but could be a pin or extend beyond a distal end of the cylinder 268. Furthermore, markings or other indicia 245 on the cylinder can more precisely show or measure the displacement of the indicator 246.

As further shown in FIGS. 5A and 5B, the clip 270 has four arms 280 which extend from a clip body 282 away from the cylinder 268. Each pair of arms 280 form a circular crux 284 in which the handle 260 engages the clip 270. The cruxes 284 formed by each pair of arms 280 of the clip 270 prevent relative movement between the housing 266 and the cutter 242. The arms 280 are resiliently deformable to accept the handle 260 in a locking engagement. Such a resiliently deformable material may be a hard plastic or a metal. It should be appreciated, however, that other mechanisms for engaging the handle 260 with the clip 270 are suitable for use in accordance with the present invention.

Referring to FIG. 10, it can be seen that the clip body 282 has a surface which defines a hole 286 perpendicular to the longitudinal axis 258. The clip body 282 can snap onto a cavity 288 (see FIG. 9) defined by the outer surface 272 in the cylinder 268 to permanently engage the clip 270 with the cylinder 268. The clip body 282 and the cylinder 268 can alternatively be constructed for temporary engagement of the clip 270 with the cylinder 268. In other alternative embodiments, the clip 270 and the cylinder 268 can be formed as an integral unit. In still other alternative embodiments of the present invention, the tool 240 (including the clip 270, the cylinder 268 and the cutter 242) can be formed as an integral unit.

In FIG. 6, the tool 240 is depicted without the cutter. It can be seen that the probe 244 extends up into the cylinder 268 at a proximal end 287 of the cylinder. FIG. 7 also shows the tool 240 without the cutter. As shown in FIG. 7, a cut-away view of the cylinder 268 reveals a biasing mechanism 290 such as a spring 290 coupled between the cylinder 268 and a distal end 292 of the probe 244. The spring 290 biases the probe 244 away from the cylinder 268 and causes the probe 244 to extend beyond the cutting portion when there is no force on the tip 264 (as shown in FIG. 5A). As further shown in the cutaway view of FIG. 7, the pin 274 is attached to the distal end 292 of the probe 244.

FIG. 8 shows an isometric view of the probe 244 for use in the present invention. As illustrated in FIG. 8, hole 294 is positioned near or in the distal end 292 of the probe 244. The hole 294 is configured such that pin 274 can be positioned therein. In this manner, the pin 274 is mounted near or in the distal end 292 of the probe 244 (as shown for example in FIG. 7) (see also Appendix I for typical dimensions and features of a tool in accordance with the present invention).

Figure 12A:
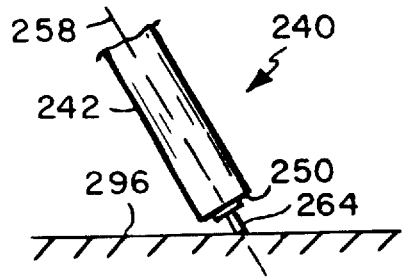
FIGS. 12A and 12B depict a cross sectional view of a cutter and a probe in contact with a bone surface at an angle other than ninety degrees with respect to the bone surface.
Figure 12B:
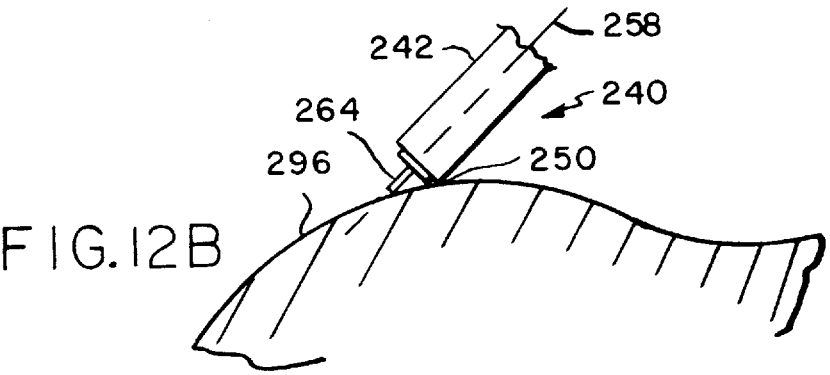

Referring now to FIGS. 12A, 12B, 13A and 13B, in use, the tool 240 is placed in contact with a bone surface 296. It is essential that the cutting portion 250 of the cutter 242 and the tip 264 of the probe 244 are in contact with the bone surface 296. As shown in FIGS. 12A and 12B, the cutter 242 and the probe 244 are both in contact with the bone surface 296. The cutter longitudinal axis 258, however, is not perpendicular with the bone surface and if a cut is made in these orientations, a non-orthogonal bone plug and hole (as depicted in FIG. 4C) will result.

Figure 13A:
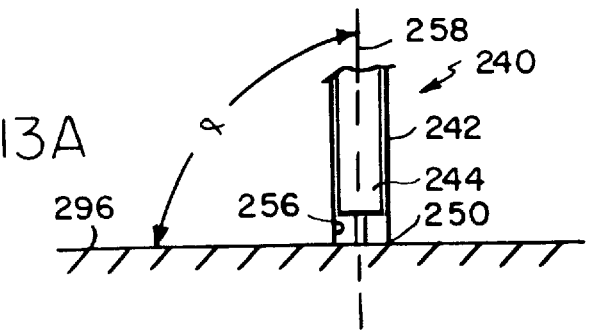
FIGS. 13A and 13B depict a cross sectional view of a cutter and a probe in contact with a bone surface.
Figure 13B:
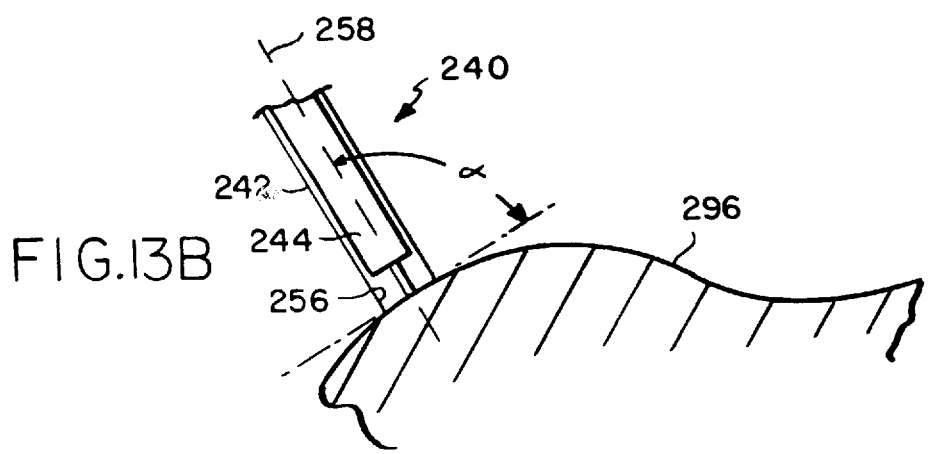

By manipulating the orientation of the tool 240, while maintaining the cutter and the probe in contact with the bone surface 296, the probe will slidably move within the bore 256 of the cutter 242 (see FIGS. 13A and 13B). The indicator (not shown in FIGS. 13A and 13B) will likewise move along the cylinder (also not shown). As the longitudinal axis 258 of the cutter 242 approaches an angle a perpendicular with the surface of the bone (and, in the case of FIGS. 12B and 13B, the surface of the bone that is local to the cutting portion), the indicator will approach its maximum displacement along the cylinder. During tool manipulation, when the indicator reaches its maximum displacement away from the bone surface, the longitudinal axis 258 of the cutter is substantially perpendicular to the bone surface 296. This is shown in FIGS. 13A and 13B where the probe 244 is at its maximum displacement relative to the cutter 242.

At this point, when the indicator is maximally displaced indicating that the longitudinal axis 258 of the cutter 242 is perpendicular to the surface of the bone 296, force is applied to the cutter 242 and a cut is made into the bone. The cut will be orthogonal to the surface of the bone and if a bone plug is cut, the bone plug will likewise be orthogonal to the surface.

In many circumstances, it is desirable that the tool of the present invention be utilized to form bone plugs orthogonal to the surface (see FIGS. 13A and 13B). In other circumstances, it may be desirable to form bone plugs at an angle other than normal to the to the surface (see FIG. 4C). However, in these circumstances, it is important to ensure that the rotational orientations are the same for the bone plug and the hole into which the plug fits.

In these latter cases, it is important that the displacement measurement of the indicator and the rotational orientation be capable of repetition. In this manner, the bone plug that is formed can be made to be compatible with the articular cartilage defect being repaired notwithstanding that the bone plug is not orthogonal to the surface being repaired. This can be accomplished by measuring the displacement of the indicator when placed in a hole formed in an articular cartilage defect, and by noting the rotational orientation of the entry point. The tool is then used to form a bone plug in which the displacement of the indicator and the rotational orientation correspond to the displacement that of the hole formed in the articular cartilage defect. In other words, the probe (and the indicator) can be indexed relative to the cutter and then the tool can be moved to other positions for use. The bone plug can then be used to repair the articular cartilage defect as described hereinabove.

It should be readily understood that the cutter 242 shown in FIGS. 5A, 5B need not be present in all embodiments. Instead, a tube without a cutting portion 250 may be used in place of the cutter. The probe and the indicator may be used to repeatably orient the tube with respect to the bone surface. Such a tube, in a configuration similar to the cutter, is orientable using the probe and the indicator in the manner described above. Upon reaching the desired orientation of the tube, the probe and the housing may be removed and a cutter or drill inserted into the tube. The cutter or drill then cuts into the bone at the desired orientation (preferably perpendicular) to the bone surface.

Referring now to FIGS. 14A–14G, an alternative embodiment of a tool suitable for use in accordance with the present invention is illustrated. The tool shown in FIGS. 14A–14G functions in a manner similar to the previously described embodiments, i.e. to provide a tool that can cut a surface such as a bone at a repeatable angle. The tool described in this embodiment includes a cutter, a harvester and an alignment gage.

As shown in FIG. 14A, a cutter 302 includes a cutting portion 304 as described hereinabove. Cutter 302 also has proximal end 306 and distal end 308. In a preferred embodiment, cutter 302 has a hollow tube configuration with an attachment mechanism 342 proximate to the distal end thereof. Mechanism 342 is adapted to engage and connect to harvester 310. FIG. 14B shows a harvester 310 having a tube 340 with a proximal end 314 and a distal end 316. Preferably, tube 340 has a hollow configuration. Harvester 310 also includes a handle 312. Handle 312 is adapted to be connected to clip 324 of alignment gage 318, preferably at or near position 315. While the handle shown in FIG. 14B forms a T-shape configuration with the tube 340, it should be appreciated that other configurations of the handle can be utilized in the present invention.

An alignment gage 318 is shown in FIG. 14C. Alignment gage 318 includes a probe 320 having a probe tip 322 extending from a proximal end 336 thereof. Probe 320 also preferably includes a biasing mechanism such as a spring for extending the probe 320 outward from the proximal end of cutter 302 when the tool is assembled as shown in FIG. 14G. The spring may be part of a biasing mechanism in housing 326 such that the probe is forced outward from the cutter as described in the previous embodiments. The probe 320 functions in a manner like that described hereinabove. The probe 320 is adapted for slidable movement relative to the cutter when the tool is assembled. The indicator, which is attached to the probe, is capable of measuring the displacement as described above.

Alignment gage 318 also includes a clip 324, which may be detachable or an integral part of the alignment gage. As also shown in FIG. 14C, clip 324 is positioned at or near a distal end 338 of probe 320. The clip 324 is connected to cylindrical housing 326. Clip 324 is adapted to attach to handle 312 of harvester 310. Indicator ring 328 is connected to housing 326 and is positioned for slidable movement on the housing. Indicia 330, 332 for indicating the displacement of the probe 322 are also provided. For example and while not to be construed as limiting, indicia 330 can designate a level line and indicia 332 can designate a full plug line.

Figure 14D:
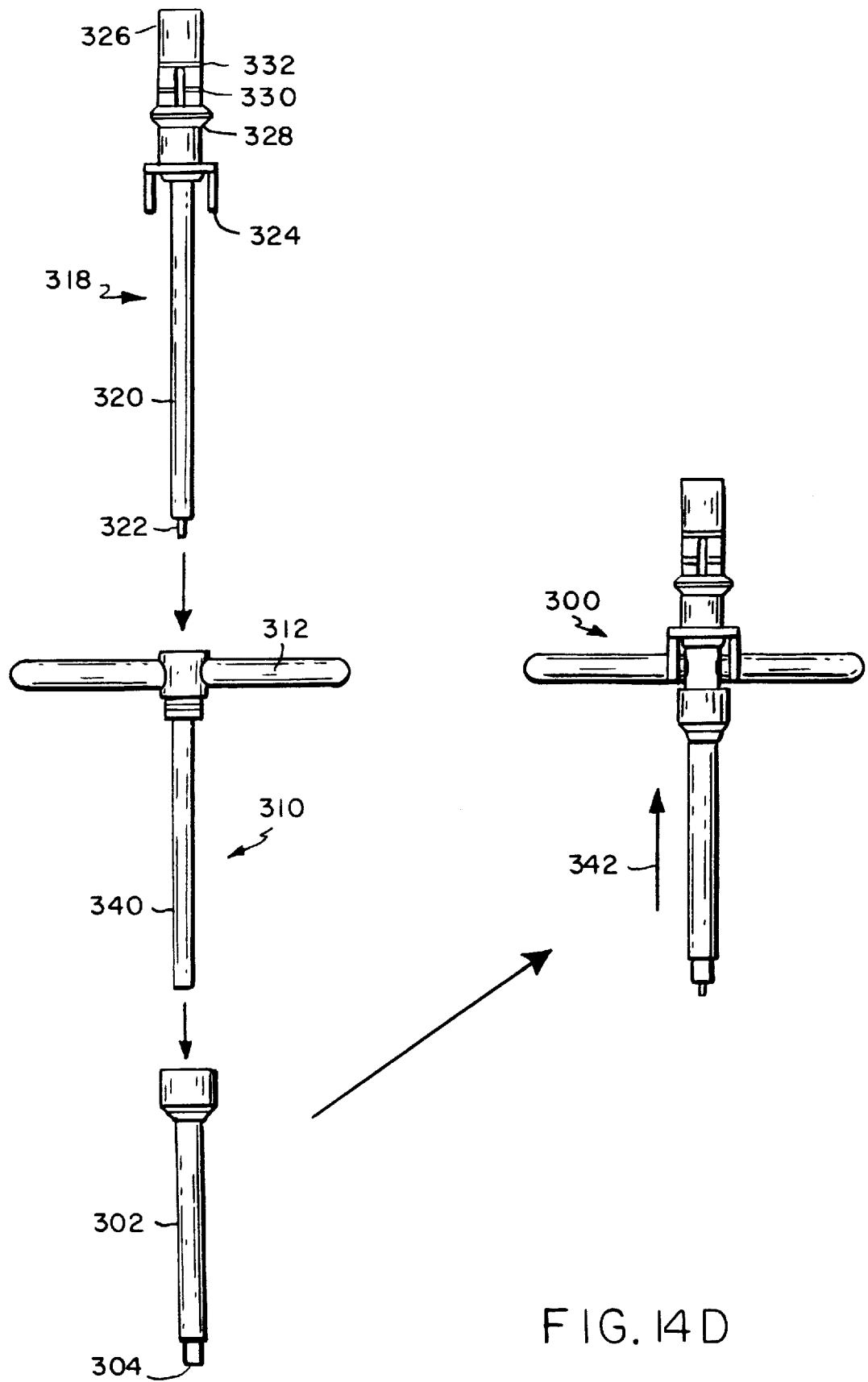

The assembly of the tool 300 can be seen in FIG. 14D. As shown, the alignment gage 318 is connected to the harvester 310 such that the probe 320 is coaxial with the tube 340 of harvester 310. As further shown in FIG. 14D, probe 320 is positioned within the tube 340. The alignment gage 318 and harvester 310 are then connected to the cutter 302. As shown, tube 340 of harvester 310 (including probe 320 and probe tip 322 of alignment gage 318) are positioned within the inner tube of cutter 302. When the assembly is complete, the biasing mechanism forces probe 320 to extend outward from the proximal end 306 of cutter 302. When a force F is applied as described above (see e.g., FIG. 5B), the probe 320 is slidably displaced relative to the cutter 302 by the force F. The probe tip 322, in turn, displaces the indicator 328 along the cylinder surface or housing 326 in the direction of arrow 342. The indicator 328 shows the relative displacement between the probe tip 322 and the cutter 302.

FIGS. 14E–14G illustrate various positions of the tool 300 when contacted with a surface to be cut, for example a bone surface 334 as shown in FIGS. 14E–14G. As shown in FIG. 14E, the cutter is angled to the bone surface 334 and the probe tip 322 is fully extended from the cutter edge. In this position, there is a relatively large gap z between the level line 330 of the indicia and the top of the indicator 328.

As the tool is rotated along the bone surface (in the direction of arrow 345), the gap can be made smaller. For example, FIG. 14F shows the cutter slightly angled relative to the bone surface and the probe tip 322 partially depressed from the cutter edge. In this position, there is a smaller gap z' (relative to gap z in FIG. 14E) between the level line 330 of the indicia and the top of the indicator 328.

As the tool is further rotated, the cutter is flush to the bone surface and the probe tip 322 is fully depressed such as that shown in FIG. 14G. In this position, there is no gap between the level line of the indicia and the top of the indicator. A bone plug can then be cut from the bone surface and used to replace an articular cartilage defect as described hereinabove.

Figure 15:
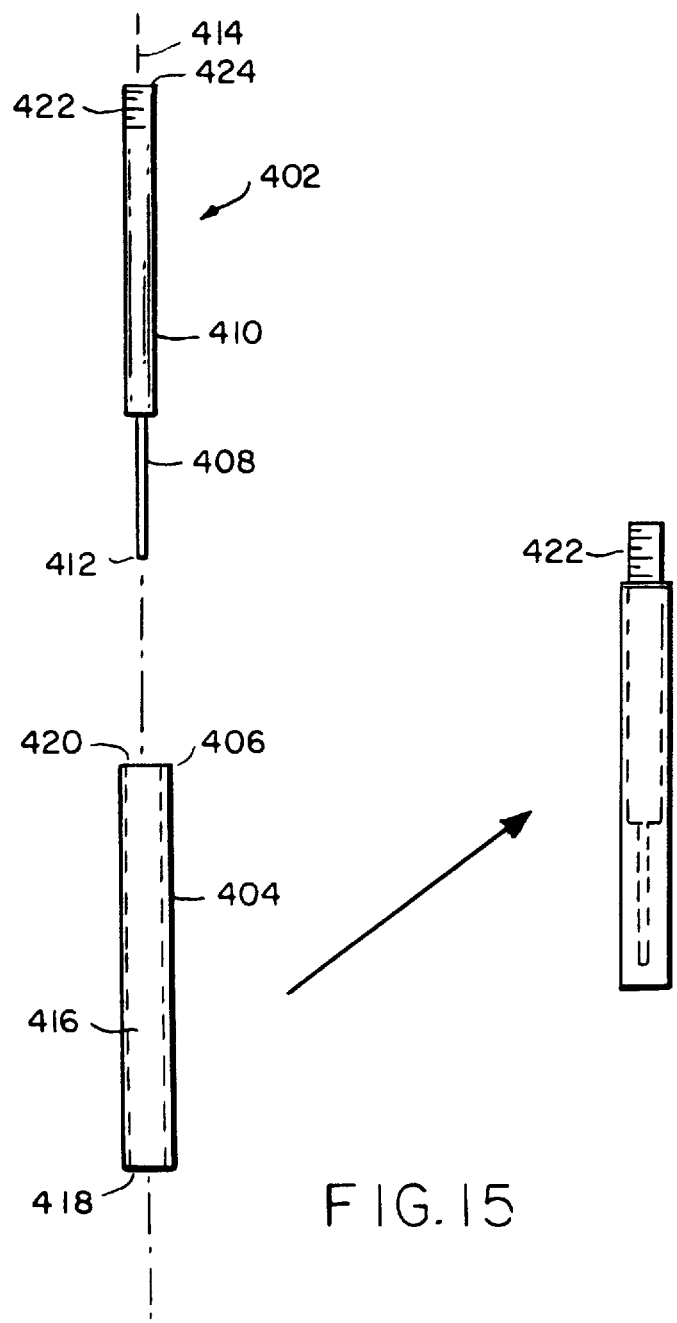
FIG. 15 illustrates another embodiment of a tool suitable for use in accordance with the invention.

Turning now to FIG. 15, another embodiment of a tool suitable for use in accordance with the present invention is illustrated. The tool shown in this FIG. 15 functions in a manner similar to the previously described embodiments and includes a drill 402, a probe 404 and an indicator 406.

The drill 402 (which may be cannulated) comprises a drill bit 408 which extends from a body 410 towards the bone surface (not shown). The drill bit 408 has a cutting end 412. The drill bit 408 is mounted in the body 410 such that the bit 408 is rotatable about an axis 414. The body 410 remains stationary with respect to the bit 408 and may contain bearings to support the bit and/or may contain a drive mechanism to turn the bit (neither shown).

The probe 404 is cylindrical and is hollow inside. A bore 416 runs the length of the probe 404 from a proximal end 418 to a distal end 420. The bore 416 is sized to accept the drill bit 408 and at least part of the body of the drill 410.

The indicator 406, in this particular embodiment, is integral to the probe 404. At the distal end 420 of the probe, the indicator 406 is located by a ring of paint or simply by the edge of the distal end 420. Indicia 422 are preferably located at a distal end 424 of the drill 402. The indicia 422 provide an index against which the relative location of the indicator 406 with respect to the drill 402 may be measured.

This particular embodiment depicted in FIG. 15 may further include elements similar to embodiments described above. Examples of these elements include, a biasing mechanism to bias the probe towards the bone surface, a housing to contain the biasing mechanism and the probe, and a clip to attach the housing to the drill (not shown). And similar to the embodiments shown in FIGS. 12A, 12B, 13A, 13B and 14E-14G, the probe and the drill are both placed in contact with a bone surface and then angularly oriented such that the indicator arrives at a desired location (not shown). Upon reaching the desired location, force may be applied to the drill and the drill bit will engage the bone surface at a desired angle. Unlike the earlier embodiments, in the embodiment depicted in FIG. 15 the probe 404 is outside the bone cutting implement (drill 402).

It should be understood by those skilled in the art that the specific embodiments disclosed above may readily be utilized as a basis for modifying or designing other methods or structures for carrying out the same purpose of the present invention. For example, the tool described hereinabove can be modified for use with other devices in which it desirable to have a cutting plane that is normal to the surface being cut. For instance, the teachings of the present invention can be used with other bone cutters, other drills and the like. Further modifications include various probe orientations and geometries (e.g., a non-cylindrical probe), and various indicating apparatuses (e.g., pins, rings, paint lines and the like). By way of further example, it will be appreciated that multiple probes may be used in accordance with the present invention. It should also be realized by those skilled in the art that such equivalent constructions do not depart from the spirit and scope of the invention as set forth in the appended claims.

What is claimed is:

1. A tool for cutting a surface comprising:
    a cutter having an operable portion for cutting the surface;
    a probe slidably disposed with respect to a longitudinal axis of the cutter for contacting the surface in a region of the operable portion of the cutter; and
    an indicator coupled to the probe, the indicator designating an angular orientation of the surface relative to the longitudinal axis of the cutter.

2. The tool according to claim 1, wherein the cutter comprises any of a cannulated drill and a cannulated rod.

3. The tool according to claim 2, wherein the operable portion of the cutter is at a proximal end of the cutter and the probe extends from beyond the proximal end of the cutter to a distal end of the cutter.

4. The tool according to claim 1, wherein the probe comprises a tip extending beyond the operable portion of the cutter.

5. The tool according to claim 4, wherein the tip of the probe is substantially coaxial with the probe.

6. The tool according to claim 5, wherein the tip extends at least 0.15 inches beyond the proximal end of the probe.

7. The tool according to claim 1, wherein the cutter includes an internal surface defining an internal bore extending along the longitudinal axis of the cutter, and a proximal end of the probe slides within the internal bore of the cutter.

8. The tool according to claim 1 further comprising biasing means coupled between a housing connected to the cutter and the probe for biasing the probe towards the surface.

9. The tool according to claim 1, further comprising a housing mounted to the bone cutter for restraining the indicator and containing a distal end of the probe.

10. The tool according to claim 9, wherein the housing includes a clip for attaching the housing on the cutter.

11. The tool according to claim 10, wherein the cutter includes a handle positioned such that the clip attaches to the handle.

12. The tool according to claim 9, wherein the housing includes a cylinder located at a distal end of the tool and adapted to receive force for driving the cutter into the surface.

13. The tool according to claim 12 wherein the indicator is a ring slidably mounted on an outside surface of the cylinder.

14. The tool according to claim 13, wherein the distal end of the probe includes a pin attached to the indicator through at least one longitudinal slot in the cylinder.

15. The tool according to claim 13, wherein the cylinder includes indicia that indicates the level of the surface contacted by the probe and designated by the indicator.

16. A tool for cutting bone comprising:
    a bone cutter having an operable portion for cutting a bone;
    a probe slidably disposed with respect to a longitudinal axis of the cutter for contacting a surface of the bone in a region of the operable portion of the bone cutter; and
    an indicator coupled to the probe, the indicator designating an angular orientation of the surface relative to the longitudinal portion of the bone cutter.

17. The tool according to claim 16, wherein the cutter comprises any of a cannulated drill and a cannulated rod.

18. The tool according to claim 17, wherein the operable portion of the cutter is at a proximal end of the cutter and the probe extends from beyond the proximal end of the cutter to a distal end of the cutter.

19. The tool according to claim 16, wherein the probe comprises a tip extending beyond the operable portion of the cutter.

20. The tool according to claim 19, wherein the tip of the probe is substantially coaxial with the probe.

21. The tool according to claim 20, wherein the tip extends at least 0.15 inches beyond the proximal end of the probe.

22. The tool according to claim 16, wherein the cutter includes an internal surface defining an internal bore extending along the longitudinal axis of the cutter, and a proximal end of the probe slides within the internal bore of the cutter.

23. The tool according to claim 16, further comprising biasing means coupled between a housing connected to the cutter and the probe for biasing the probe towards the surface.

24. The tool according to claim 16, further comprising a housing mounted to the bone cutter for restraining the indicator and containing a distal end of the probe.

25. The tool according to claim 24, wherein the housing includes a clip for attaching the housing on the bone cutter.

26. The tool according to claim 25, wherein the bone cutter includes a handle positioned such that the clip attaches to the handle.

27. The tool according to claim 24, wherein the housing includes a cylinder located at a distal end of the tool and adapted to receive force for driving the bone cutter into the bone.

28. The tool according to claim 27, wherein the indicator is a ring slidably mounted on an outside surface of the cylinder.

29. The tool according to claim 28, wherein the distal end of the probe includes a pin attached to the indicator through at least one longitudinal slot in the cylinder.

30. The tool according to claim 28, wherein the cylinder includes indicia that indicate the level of the surface contacted by the probe and designated by the indicator.

31. A tool for cutting bone in a direction substantially normal to a bone surface comprising:
   a cylindrical bone cutter having an operable portion at a proximal end for cutting the bone;
   a probe mounted within the cutter and slidable along a longitudinal axis of the cutter for contacting the bone surface;
   a cylindrical housing connected to a distal end of the probe;
   biasing means coupled between the cylindrical housing and the probe for biasing the probe beyond the proximal end of the cutter towards the bone surface;
   an indicator connected to an outside surface of the cutter and connected to the cylindrical housing, the indicator slidably movable along the bone cutter and the cylindrical housing; and
   a pin disposed within a longitudinal slot in the cutter, the pin connecting the probe to the indicator;
   wherein when the probe and the operable portion of the cutter are in contact with the bone surface, a longitudinal axis of the cutter is approximately perpendicular to the bone surface when the indicator is maximally displaced away from the proximal end of the cutter.

32. The tool of claim 31, wherein the probe includes a body and a tip, the probe tip extending beyond a proximal end of the probe body towards the bone surface.

33. The tool of claim 32, wherein the tip is coaxial with the longitudinal axis of the cutter.

34. The tool of claim 33, wherein the tip extends at least 0.15 inches beyond the proximal end of the probe.

35. The tool of claim 34, wherein the tip is cylindrical and has a diameter less than 0.06 inches.

36. A tool for cutting bone comprising:
   a drill having a drill bit with an operable portion for cutting the bone;
   a probe surrounding the drill bit and slidable with respect to the bit along a longitudinal axis of the bit for contacting a surface of the bone in a region of the operable portion of the bit; and
   an indicator coupled to the probe, the indicator designating an angular orientation of the surface relative to the longitudinal axis portion of the bit.

37. The tool according to claim 36, wherein the operable portion of the bit is at a proximal end of the bit and the probe is extendable beyond the proximal end of the bit.

38. The tool according to claim 36, wherein the probe comprises a cylinder having an internal surface defining a bore which extends from a proximal end to a distal end of thereof.

39. The tool according to claim 38, wherein the bit is arranged within the bore of the probe.

40. The tool according to claim 39, further comprising biasing means coupled between a housing connected to the drill and the probe for biasing the probe towards the surface.

41. The tool according to claim 36, further comprising a housing mounted to the drill for restraining the indicator and containing a distal end of the probe.

42. The tool according to claim 41, wherein the housing includes a clip for attaching the housing on the drill.

43. The tool according to claim 41, wherein the housing includes indicia that indicates the level of the surface contacted by the probe and designated by the indicator.

44. A tool for orientation on a bone surface comprising:
   a tube cutting having a first end for contacting the bone surface;
   a probe slidably disposed with respect to a longitudinal axis of the tube for contacting a surface of the bone in a region of the first end of the tube; and
   an indicator coupled to the probe, the indicator designating an angular orientation of the relative to a surface of the bone the longitudinal axis of the tube.

45. The tool according to claim 44, wherein the tube is cylindrical.

46. The tool according to claim 45, wherein the probe extends beyond the first end of the tube towards the bone surface.

47. The tool according to claim 45, wherein the probe comprises a tip and a body, the tip extending beyond the first end of the tube.

48. The tool according to claim 47, wherein the tip of the probe is substantially coaxial with the probe.

49. The tool according to claim 48, wherein the tip extends at least 0.15 inches beyond the body of the probe.

50. The tool according to claim 44, wherein the tube includes an internal surface defining an internal bore extending along a longitudinal axis of the cutter, and a proximal end of the probe slides within the internal bore of the tube.

51. The tool according to claim 50, wherein the probe is removable from the bore of the tube such that an instrument may be placed within the bore.

52. The tool according to claim 51, wherein the instrument comprises any of a cannulated drill and a cannulated rod.

53. The tool according to claim 44, further comprising biasing means coupled between a housing connected to the tube and the probe for biasing the probe towards the bone surface.

54. The tool according to claim 44, further comprising a housing mounted to the tube for restraining the indicator and containing a distal end of the probe.

55. The tool according to claim 54, wherein the housing includes a clip for attaching the housing on the tube.

56. The tool according to claim 55, wherein the tube includes a handle positioned such that the clip attaches to the handle.

57. The tool according to claim 56, wherein the indicator is a ring slidably mounted on an outside surface of the cylinder.

58. The tool according to claim 57, wherein the distal end of the probe includes a pin attached to the indicator through at least one longitudinal slot in the cylinder.

59. The tool according to claim 58, wherein the cylinder includes indicia that indicates the level of the surface contacted by the probe and designated by the indicator.

60. A tool for cutting a surface comprising:
   a cutter having an operable portion for cutting the surface;
   a plurality of probes slidably disposed with respect to a longitudinal axis of the cutter for contacting the surface in a region of the operable portion of the cutter; and
   an indicator coupled to at least one of the probes, the indicator designating an angular orientation of the surface contacted by that probe relative to the longitudinal axis of the cutter.

61. The tool according to claim 60, wherein the operable portion of the cutter is at a proximal end of the cutter and at least one of the probes extends from beyond the proximal end of the cutter to a distal end of the cutter.

62. The tool according to claim 60, wherein at least one of the probes comprises a tip extending beyond the operable portion of the cutter.

63. The tool according to claim 62, wherein the tip of the at least one probe is substantially coaxial with that probe.

64. The tool according to claim 63, wherein the tip extends at least 0.15 inches beyond the proximal end of the at least one probe.

* * * * *